United States Patent [19]
Hugl et al.

[11] Patent Number: 5,194,393
[45] Date of Patent: Mar. 16, 1993

[54] OPTICAL BIOSENSOR AND METHOD OF USE

[75] Inventors: Herbert Hugl, Bergisch Gladbach, Fed. Rep. of Germany; Eberhard Kuckert, West Haven, Conn.; Dietmar Möbius, Waake, Fed. Rep. of Germany; Holger Ohst, Odenthal, Fed. Rep. of Germany; Meinhard Rolf, Charlston, S.C.; Hans J. Rosenkranz, Krefeld, Fed. Rep. of Germany; Heinrich C. Schopper, Krefeld, Fed. Rep. of Germany; Hans-Ulrich Siegmund, Krefeld, Fed. Rep. of Germany; Klaus Sommer, Cologne, Fed. Rep. of Germany; Rolf Wehrmann, Krefeld, Fed. Rep. of Germany

[73] Assignee: Bayer Aktiengesellschaft, Leverkusen, Fed. Rep. of Germany

[21] Appl. No.: 611,197

[22] Filed: Nov. 8, 1990

[30] Foreign Application Priority Data

Nov. 21, 1989 [DE] Fed. Rep. of Germany ....... 3938598
Apr. 28, 1990 [DE] Fed. Rep. of Germany ....... 4013713

[51] Int. Cl.$^5$ .......................................... G01N 33/553
[52] U.S. Cl. .................................... 436/525; 436/527; 436/531; 436/805; 436/800; 422/82.08; 422/82.11; 435/968
[58] Field of Search ................... 435/4, 173, 291, 808, 435/968; 422/57, 60, 58, 82.08, 82.05, 82.07, 82.11; 436/537, 172, 805, 807, 525, 527, 531, 800; 250/458.1, 459.1, 461.1, 483.1, 486.1

[56] References Cited

U.S. PATENT DOCUMENTS

| | | | |
|---|---|---|---|
| 4,261,968 | 4/1981 | Ullman et al. | 436/537 |
| 4,777,128 | 10/1988 | Lippa | 436/537 |
| 4,820,649 | 4/1989 | Kawaguchi et al. | 422/57 |
| 5,037,615 | 8/1991 | Kane | 422/82.08 |

FOREIGN PATENT DOCUMENTS 0150905 7/1985 European Pat. Off. .
0174744 3/1986 European Pat. Off. .

OTHER PUBLICATIONS

WPIL. File Supplier, AN=88-033622, Derwent Publications Ltd. London.
Chemical Abstracts, vol. 112, No. 4, Jan. 22, 1990, p. 631 Zusammenfassung No. 29895n.
Chemical Abstracts, vol. 110, No. 6, Feb. 6, 1989, p. 787, Zusammenfassung No. 50443g.
Nature, vol. 320, No. 13, Mar. 1986, pp. 179-181, London.
Annual Reviews of Biochemistry, Bol. 47, 1978, pp. 819-846, Palo Alto, Calif.

Primary Examiner—Robert J. Warden
Assistant Examiner—William H. Beisner

[57] ABSTRACT

The present invention relates to a sensor with a novel construction for a detection method of molecules labelled with fluorescent dye for detecting these dissolved substances or analytes by energy transfer with a simple fluorescence technique and increased sensitivity in the detection as well as versatile use for different tasks and the possibility of reproducible preparation of films bound to solid surfaces.

12 Claims, 1 Drawing Sheet

OPTICAL BIOSENSOR AND METHOD OF USE

BACKGROUND OF THE INVENTION

1. Field of the Invention

The present invention relates to an optical biosensor with a novel construction for a detection method for molecules which are labelled with a fluorescent dye for the detection of dissolved substances or dissolved analytes which behave, for example, like antigen and antibody. This takes the form of a solid-phase sensor with fluorescent dye which permits an energy-transfer process to a molecule which is to be detected and is labelled with a second fluorescent dye.

2. Description of the Related Art

There are various methods for detecting analytes such as hormones, enzymes, other proteins, carbohydrates, nucleic acids, pharmacological active compounds, toxins and others in liquid samples of biological origin. Among the known methods, immunoassays in particular are outstanding as a sensitive detection method for the determination of very small amounts of organic substances. Immunoassay methods are generally based on the ability of a receptor molecule, for example of an antibody, to recognise specifically the structure and molecular organization of a ligand molecule, whether it is defined by non-polar and/or polar interactions, and to bind this molecule very specifically in such a manner.

Immunoassays are carried out by various methods. These include the use of various labelling techniques, usually of a radioactive, enzyme-coupled and fluorescent nature too (Methods in Enzymology, 74 (1981), 28–60).

Some of these known immunoassay methods entail the use of fluorescent dye molecules $F_1$ which are able to absorb light of a wavelength $\lambda_1$ and to emit light of a second, larger wavelength $\lambda_2$. Under certain conditions, in the presence of another fluorescent dye molecule $F_2$, excitation of $F_1$ by light of the wavelength $\lambda_1$ is followed by a radiationless energy transfer to $F_2$ which then in turn emits light of a third, even larger wavelength $\lambda_3$.

This principle of energy transfer has been described in theory by Förster and has been the stimulus for a wide variety of possible applications (Annual Reviews in Biochemistry 47 (1978), 819–846). One important property of this energy transfer is its dependence on distance. The efficiency of energy transfer according to Förster is described by the critical radius $R_o$, namely the distance between donor and acceptor at which the intermolecular energy transfer is of equal probability to the total of all other inactivating processes of the donor. This distance is about 50–100 Å.

Immunoassays which are based on exploitation of the distance-dependent energy transfer have already been described. Thus, EP 150,905 describes an immunoassay operating in homogeneous solution, in which analyte or antigen has been labelled with a fluorescent dye $F_1$ and the antibody which binds specifically thereto has been provided with a fluorescent dye $F_2$. In order to detect the specific binding, and thus as analytical method, use is made of the fact that when light of wavelength $\lambda_1$ is passed in, emission of the wavelength $\lambda_3$ can be observed only if analyte and antibody are present in sufficient concentration at a distance which is sufficiently small for energy transfer according to Förster. This is the case only when analyte and antibody have entered into specific binding.

In another example, one of the two labelled binding partners is attached to a solid surface, and the correspondingly specifically binding partner is bound from a homogeneous solution. Once again the specific binding is detected as already explained above by an appropriate energy transfer by means of evanescent wave technology (Nature 320 (1986), 179–181).

Both the energy transfer in homogeneous solution, which is mentioned here, and the described solid-phase immunoassay with energy transfer have the disadvantage in principle that the molecules which bind specifically with one another have in each case to be labelled with one of the two necessary fluorescent dyes $F_1$ and $F_2$ and, according to Nature 320 (1986), 179–181, allow a maximum $F_1:F_2$ ratio of 2:1.

Methods with which the sensitivity, which is limited by the ratio of the two fluorescent dyes $F_1$ and $F_2$, of the fluorescent-spectroscopic detection can be improved have already been described. Thus, it is proposed in EP 174,744 that several organic dye molecules be covalently bonded simultaneously to one "light-collecting" protein, that is to say energy transfer of several organic dye molecules to only one acceptor molecule takes place, namely a phycobiliprotein (allophycocyanin) in EP 174,744. This molecular system is then in turn proposed as a "marker" for other biological molecules. The method is limited by the dye:protein coupling ratio.

A further disadvantage of the stated systems derives from the fact that complementary systems have in each case to be specifically labelled and thus versatile use is impossible. Another disadvantage of these systems constructed in heterogeneous phase is the specific evanescent wave technique used. Moreover, the immobilization of the specifically binding molecules to the solid surface via a coupling component/antibody/antigen-/antibody system entails very elaborate preparation. Another disadvantage in principle of this solid-phase technology in immunoassays is the reproducible preparation of coatings of the assay matrix with the reactants in the immune reaction. However, besides sensitivity and selectivity for a target substance, an essential quality feature for analytical methods is the reproducibility of the detection method.

SUMMARY OF THE INVENTION

The present invention relates to a sensor with a novel construction for a detection method of molecules labelled with fluorescent dye for detecting these dissolved substances or analytes by energy transfer with a simple fluorescence technique and increased sensitivity in the detection as well as versatile use for different tasks and the possibility of reproducible preparation of films bound to solid surfaces. Besides the distinct increase in sensitivity, all the disadvantages listed above are simultaneously avoided.

The invention relates to an optical biosensor based on fluorescence energy transfer, consisting of
- a) a solid support,
- b) a single-layer or multilayer Langmuir-Blodgett (LB) film attached to a),
- c) at least one fluorescent dye $F_1$ which is located in at least one of the top 4 layers of the LB film,
- d) a receptor molecule which is capable of specific interaction and which is bound or located in or on the topmost layer of the LB film, and e) a mobile fluorescent dye $F_2$ whose excitation band overlaps, sufficiently for an energy transfer, with the emission band of $F_1$ and which e1) is covalently bonded to a ligand which is able to bind to the receptor, or which e2) is covalently bonded to another receptor which is able to bind to the complex composed of the first receptor and ligand, where the ligand or the ligand and the second receptor are initially not bound to the LB film.

DETAILED DESCRIPTION OF THE INVENTION

Figure 1:
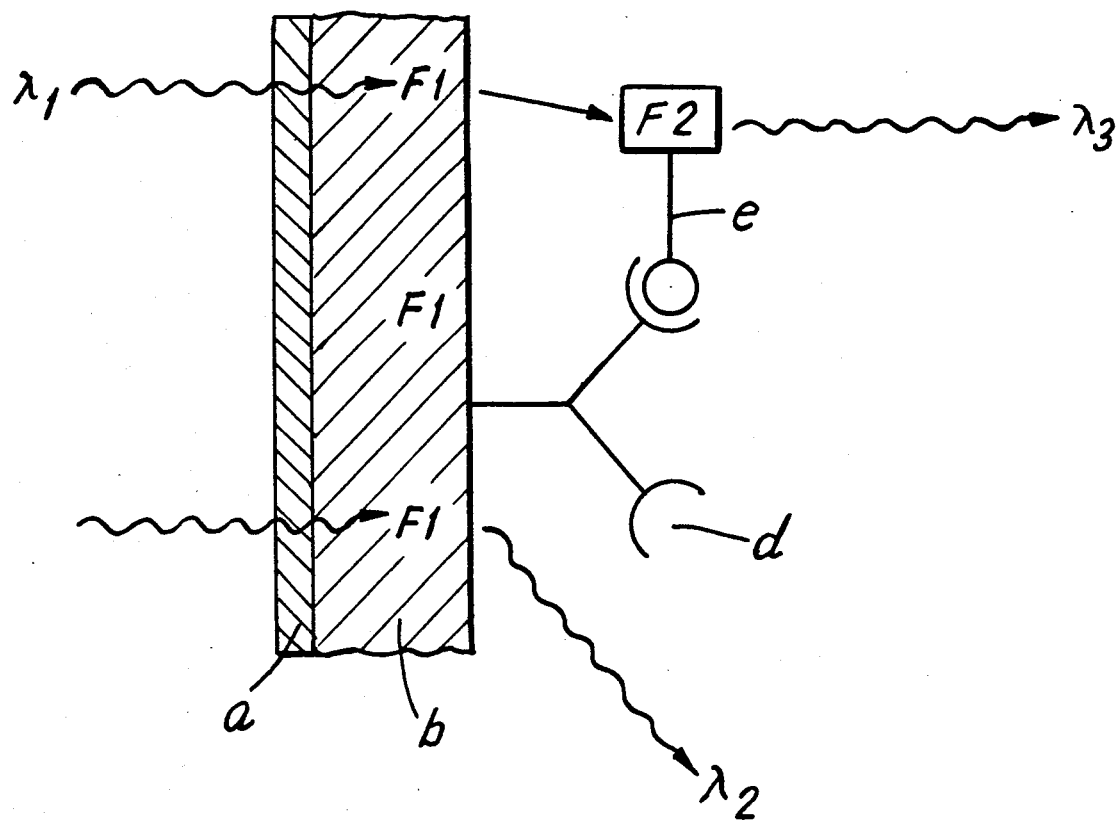
FIG. 1 is a schematic representation of the optical biosensor of the present invention.

Suitable supports are all supports which are known to the skilled worker and are suitable for the LB technique, such as glass, quartz glass, other glasses such as Li niobate, zinc selenide, porcelain, semiconductor materials such as germanium, GaAs or silicon, and metals.

Also suitable are: plastics such as polymethylmethacrylate, polycarbonate, polystyrene and others, and metallized plastics. The solid support materials can also be surface-modified before the coating, for example glass or quartz or silicon by pretreatment with trichloromethylsilane, dichlorodimethylsilane, trichlorooctadecylsilane, hexamethyldisilazane or by plasma etching or plasma polymerization. In a preferred manner, the supports take the form of optionally surface-modified glass, quartz glass, silicon, plastic or a metallized plastic. Other preferred supports are optically transparent. All support materials are additionally distinguished by a uniform surface, preferably by a plane surface.

One or more monomolecular films are applied to such supports with the aid of the LB technique. The LB technique means hereinafter a process for transferring monomolecular films from a liquid (water) surface to a solid support by the Langmuir-Blodgett process. For this, a solid support with an essentially smooth surface is dipped in a manner known per se through a compressed monomolecular film on the liquid surface and, in this way, this film is transferred to the support.

It is possible in this way to prepare multilayer systems by multiple immersion and emergence. The film on the liquid surface can be replaced after each dipping procedure so that different sequences of films can be prepared on the support.

The immersion and emergence can take place at right angles or obliquely to the liquid surface. Furthermore, it is possible according to the Langmuir-Schäfer technique for the support also to be contacted at a point or at an edge with the liquid surface and then pivoted onto the liquid surface. Finally, the support can also be lowered onto the liquid surface in a parallel manner ("horizontal dipping").

The transfer takes place at a temperature of 5°–40° C., preferably at room temperature.

These ordered LB films can consist of low molecular weight and/or polymeric amphiphiles, preferably of polymeric amphiphiles, and can contain covalently bonded fluorescent chromophore/dyes and/or amphiphilic fluorescent chromophore/dyes, which are called $F_1$ hereinafter.

These LB films additionally contain or are covalently linked to functional molecules as receptors, for example glycolipids, poly- and oligonucleotides, proteins or fragments thereof, haptens and others. It is now possible for a specific binding to these receptors to take place by a molecule complementary thereto (ligand), such as by a lectin, an antigen, an antibody and others, which is labelled with a second fluorescent dye $F_2$ appropriate for energy transfer with $F_1$. In the case of binding between receptor and ligand, the so-called Förster distance between $F_1$ and $F_2$, as is necessary for the energy transfer described above, ought to be complied with. This condition is ensured by the use of the LB technique which allows a specific molecular architecture, especially in dimensions of the range of interest here, of about 10–100 Å. If the system described hereinbefore is now excited with light of the wavelength $\lambda_1$, it is possible to detect an emission of the fluorescent dye $F_2$ with a wavelength $\lambda_3$, which is regarded as demonstrating the binding of the molecule labelled with $F_2$ to the sensor surface which is doped with $F_1$. Excitation with light of the wavelength $\lambda_1$ can be carried out in such a way that $F_1$ in the LB film is excited by transmission through the optically transparent support or by evanescent wave technique, when the optically transparent support acts as light guide, or else by incident irradiation.

The specific interaction between 2 molecules which are complementary to one another is known to the skilled worker in the field of biologically, bio-chemically and, very particularly, medically (physio-logically) important molecules, for example of the abovementioned type. Such interactions derive in the final analysis from ionic linkages, hydrogen bonds and van der Waals forces, which are, however, effective in the area of the abovementioned molecules only with specific spatial (steric) circumstances (lock and key theory). It is, of course, also possible to use the optical biosensor according to the invention for detecting specific interactions without such specific spatial circumstances; this use is particularly important for checking the reliability of functioning, the accuracy of measurement and other properties of the optical biosensor according to the invention.

The sensor construction described in this way is able in this function to detect not only an analyte present in solution and labelled with a fluorescent dye $F_2$; the sensor construction can also be used to detect in a competitive mode of functioning an analyte which is not fluorescent-labelled. For this purpose, when preparing the sensor, the specific binding sites of the functional molecules in the LB film are saturated with fluorescent-labelled molecules which bind complementarily. Then, on excitation with light of the wavelength $\lambda_1$ there is observed a maximum fluorescence emission of the wavelength $\lambda_3$, whose decrease over a time course can be observed when, on contact with the solution to be investigated, the molecules which are fluorescent-labelled with $F_2$ and bind complementarily are displaced in an equilibrium reaction by molecules of the same type which are not fluorescent-labelled and bind complementarily.

Amphiphilic molecules, that is to say molecules which have a hydrophilic end (a "head") and a hydrophobic end (a "tail") are used for constructing LB films. Such amphiphilic molecules can be low-molecular weight compounds with a molecular weight of up to about 2000 g/mol. In another variant, these low molecular weight amphiphiles can contain functional groups which are capable of polymerization or capable of polycondensation and polyaddition so that, after construction of the LB films from low molecular weight amphiphiles, these amphiphiles in the LB film can be linked in a subsequent reaction to give high molecular weight compounds. This subsequent reaction to give high molecular weight compounds is advantageous because LB films composed of polymeric amphiphiles have higher thermal and mechanical stabilities.

It is possible particularly elegantly to prepare LB films from amphiphilic polymers by bringing about the linkage of the amphiphilic units before the latter are spread in a known manner on the liquid surface to give monomolecular films. The use of such prepolymerized amphiphilic polymers thus avoids possible disturbance, by subsequent polymerization in the LB film, of the ordered state once it has been produced.

Examples of polymeric amphiphiles as are suitable for the optical biosensor according to the invention are a-olefin/maleic anhydride copolymers (British Polymer Journal 17 (1985), 368 et seq.; J. Macromol. Sci. Phys. B 23 (1985), 549-573), polyoctadecylmethacrylate, polyvinyl stearate (J. Coll. Interface Sci. 86 (1982), 485), polyvinylphospholipids (Angew. Chem. 100 (1988), 117-162), cellulose tristearate, amphiphilic polyamides (DE-OS (German Published Specification) 3,830,325) and acrylamide copolymers. Suitable and preferred for the preparation of stable LB films are polyurethanes according to DE-OS (German Published Specification) 3,827,438 and polyesters according to DE-OS (German Published Specification) 3,830,862. Among the polymeric amphiphiles, reference may also be made very especially to random poly(alkyl methacrylate) copolymers of the following type, whose composition can vary widely:

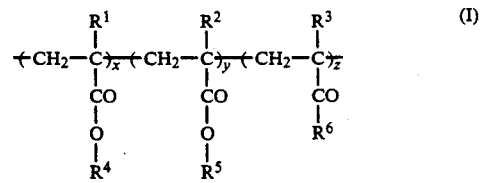

in which
$R^1$, $R^2$ and $R^3$ represent, independently of one another, hydrogen or methyl,
$R^4$ is straight-chain $C_{14}$-$C_{22}$-alkyl,
$R^5$ is the hydrogen, sodium or potassium ion or represents one of the groups —$CH_2$—$CH_2OH$, —$CH_2$—$CH_2$—NH-tertbutyl, —$CH_2$—$CH_2$—$N(CH_3)_2$,

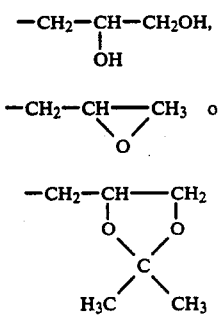

$R^6$ is a fluorescent chromophore which is known to the skilled worker and is represented hereinafter, and
x assumes a value of 0.2–1,
y assumes a value of 0–0.8 and
z assumes a value of 0–0.2, where the total x+y+z=1.

In a preferred manner, x and y are approximately equal.

Examples of polymers of the formula (I) are the following:

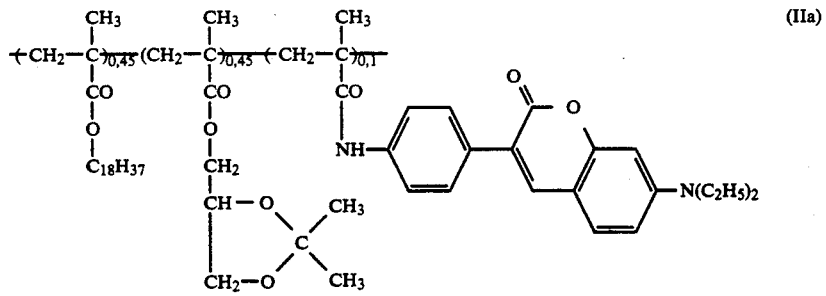

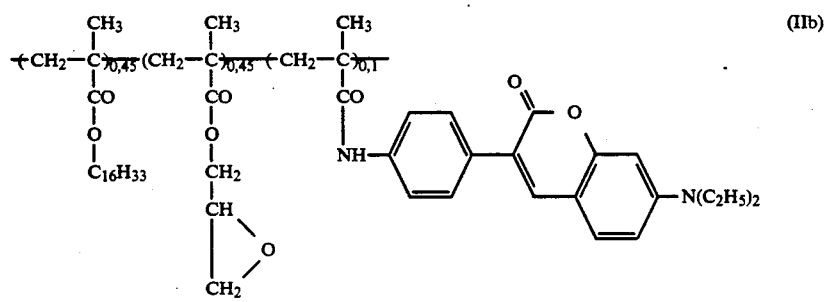

In the case of the substances mentioned here by way of example for LB mono- and -multifilms, the fluorescent chromophore is covalently linked to the amphiphilic polymer. Although this arrangement allows the maximum possible stability of the $F_1$-containing LB films, it is also possible, however, to obtain $F_1$-containing LB films by spreading an amphiphilic polymer together with amphiphilic fluorescent dyes on the water surface before the coating process. Examples of such amphiphilic fluorescent dyes which can be used together with amphiphilic polymers which contain no chromophores are, for example, cyanine dyes of the types

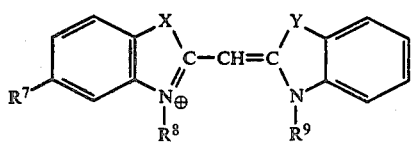 (IIIa)

and

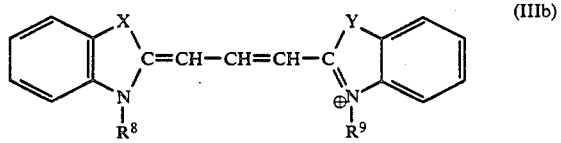 (IIIb)

in which

X and Y represent, independently of one another, oxygen, sulphur or selenium or $C(CH_3)_2$, $R^7$ denotes hydrogen or methyl, and $R^8$ and $R^9$ represent, independently of one another, straight-chain $C_1$-$C_{22}$-alkyl.

Further examples of fluorescent dyes which are known in principle to the skilled worker and can be used according to the invention are dyes of the following types:

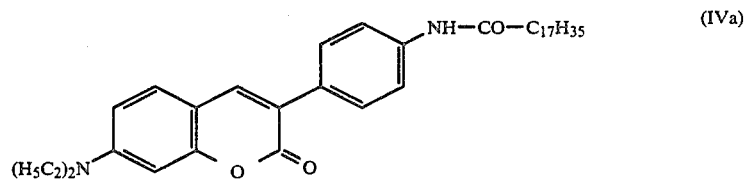 (IVa)

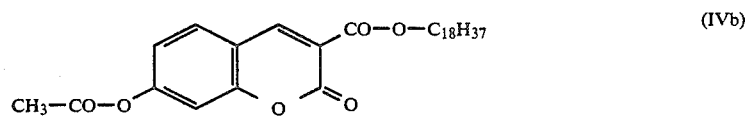 (IVb)

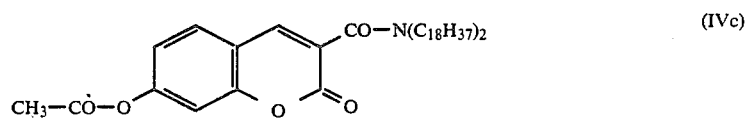 (IVc)

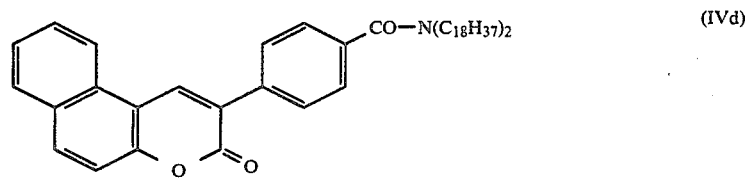 (IVd)

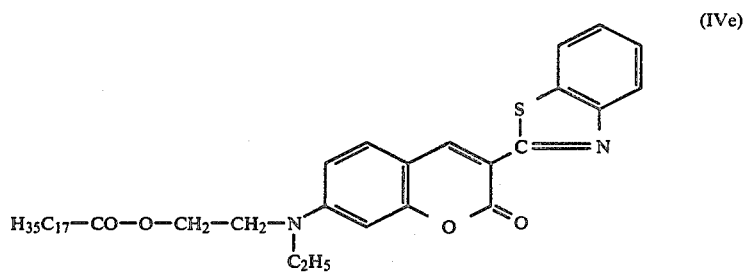 (IVe)

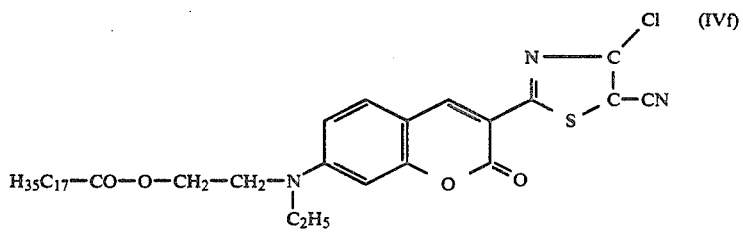 (IVf)

-continued

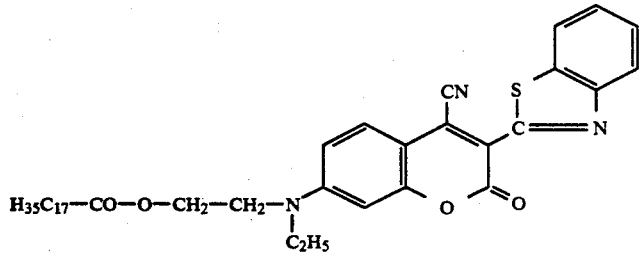 (IVg)

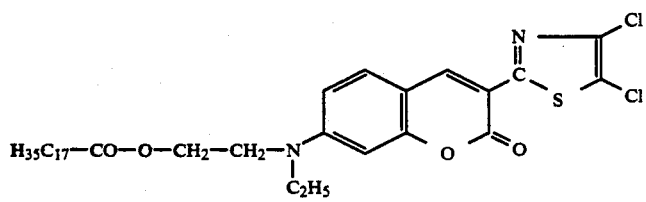 (IVh)

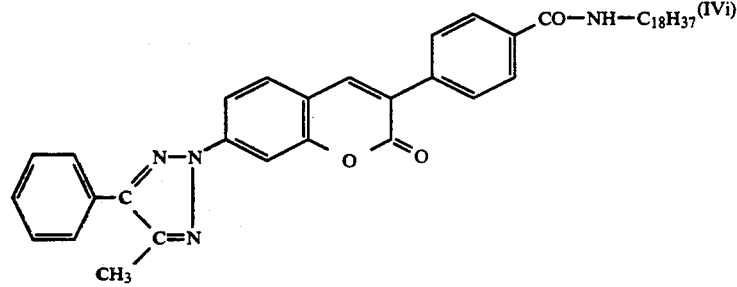 (IVi)

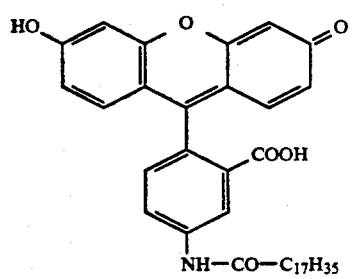 (IVj)

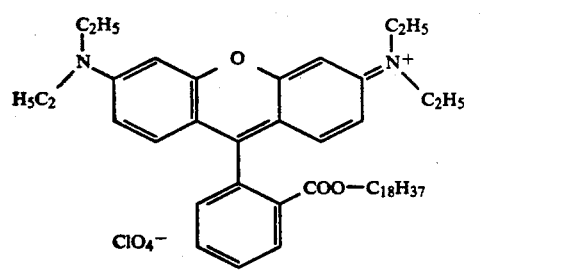 (IVk)

This list is only by way of example. Further amphiphilic fluorescent dyes are described in the monograph Physical Methods of Chemistry, Vol. 1, Part. 3B, pages 577 et seq., John Wiley, New York 1972. If the intention is to introduce such amphiphilic fluorescent dyes into LB films, care must be taken that there is uniform distribution of the dye throughout the film. Thus, it is necessary to avoid the transfer of individual films taking place, depending on the temperature (typically 5°–40°, preferably about 20° C.), with such an applied thrust at which a coexistence region of the solid-analogous and liquid-analogous phase is passed through. This is important because the amphiphilic fluorescent dye does not, as a rule, have the same solubility in both phases and thus inhomogeneous films, which are less suitable for the sensor application, are formed. This phenomenon is known for LB films composed of low molecular weight substances (Angew. Chem. 100 (1988), 750); this phenomenon has also been observed for polymerized phospholipids (Polymer Sci. 267 (1989), 97–107).

It has been found in the production of optical biosensors according to the invention, surprisingly, that LB films composed of polymers of the formula (II) do not tend to form phase-separated domains when thrusts are applied up to collapse of the LB film at >45 mN/m thrust. Besides polymers of the formula (II), this also applies to a mixture of a polymer of the type of the formula (V) and of a dye, for example of the formula (IVa), where the polymer of the type of the formula (V) is to be regarded as "matrix" in which 0.1 to 25 mol-% of the amphiphilic dye can be accommodated, where the repeat units are used for calculating the molar percentages in the polymer:

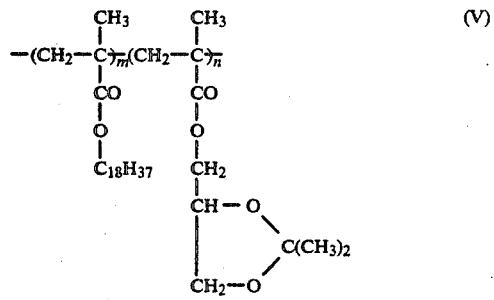

in which
  m assumes values of 0.25-1 and
  n assumes values of 1-m.

In a preferred manner, m assumes values of 0.4-0.6.

LB films produced in this way have films which are homogeneous under the light microscope, both on water as subphase and after transfer to a solid support, and are without defects and are particularly suitable for the biosensors according to the invention.

However, in the case of systems with phase-separated domains, it is also possible to achieve a high sensitivity of the optical biosensor according to the invention when fluorescent dyes $F_1$ are used as donor in LB films which, by reason of their specific behaviour, form aggregates with fluorescent-spectroscopic properties which differ greatly from those of the monomeric dye and which, as a rule, are distinguished by a correspondingly sharper and more intense absorption band and correspondingly sharper and more intense fluorescence emission band. Aggregates of this type are known to the skilled worker as J-aggregates or Scheibe-aggregates (Physical Methods of Chemistry, Vol. 1, Part. 3B, page 579, John Wiley, New York 1972). With the specific behaviour of such J aggregates, it is possible on the one hand to achieve a very high dye density $F_1$ in the LB films, and on the other hand to achieve, by reason of the strong absorption of light of the wavelength $\lambda_1$, a high energy density which, according to the theory of Förster, can be transferred to appropriate molecules $F_2$. The small half-width of the emission band means both an amplifying effect on the measured signal and a reduction in the interfering radiation owing to less overlap of the emissions of $F_1$ with $F_2$.

Fluorescent dyes which are able to form J-aggregates in LB films have been described in the abovementioned literature. Examples which may be mentioned are cyanine dyes and merocyanines.

The incorporation of functional molecules into the LB film containing the fluorescent dye $F_1$ can be carried out in a variety of ways:

The functional molecule can be linked covalently, where appropriate using spacer molecules, to the LB film, whether from the start of the spreading process on the water surface onwards or by a subsequent coupling reaction to the LB film either on the subphase or after application of the LB film to a solid support.

The functional molecule can be spread together as amphiphile and thus incorporated physically with "anchor" into the LB film.

Methods are known from the literature for both incorporation variants. For example, the linkage of biological functional groups to LB films on solid supports can be carried out in a manner analogous to the immobilization methods known to the skilled worker from biochemistry (Methods in Enzymology, Vol. 135 and Vol. 136 (1987)). A large selection of molecules provided with long alkyl chains is mentioned in DE-OS (German Published Specification) 3,546,150 as membrane anchor-active compound conjugates, and they can be incorporated into the LB film by spreading together on the subphase. Glycolipids, for example ceramides, may be mentioned as an example of such amphiphilic functional molecules. Other examples are antibody/antigen systems as well as complementary nucleotide sequences. A large number of such examples is known to the skilled worker (Angew. Chem. 100 (1988), 117–162).

Crucial for the increase in the sensitivity of the sensor system is a highest possible $F_1:F_2$ ratio within the "Förster radius" and thus a corresponding enhancement of the fluorescent signal of a molecule labelled with $F_2$ after binding has taken place to a surface doped with $F_1$. Accordingly, it is advantageous to introduce the maximum number of $F_1$ chromophores into the topmost LB films, especially into the topmost four layers. In a particularly preferred manner, the dye $F_1$ is located in at least one of the two upper layers.

Although fluorescent dye concentrations below 1% are normally used in fluorescence spectroscopy in order to avoid interactions between the individual dye molecules and thus changes in their fluorescent behaviour, it is nevertheless advantageous in the optical biosensor according to the invention to introduce the fluorescent dye $F_1$ in high concentrations into the LB films. In particular, polymeric amphiphilic fluorescent dyes show less of a tendency to self-quenching and excimer formation at dye concentration of 0.1-25 mol-%. The same concentration range has also proved advantageous in the case where isolated chromophores are to be uniformly distributed in the LB film. On the other hand, in the particular case of Scheibe-aggregates the association of chromophores is desired. This association takes place preferentially at dye concentrations above 25 mol-% up to 100 mol-% (without polymeric matrix).

The optical biosensor according to the invention additionally has the advantage that, irrespective of the functional molecules introduced into the films of the solid phase, the dye $F_1$ which is required for the principle of energy transfer can be introduced into the LB film freely selectably in wide spectral ranges. This means that, on the one hand, the functional molecule does not have to be specifically labelled with $F_1$ and, on the other hand, the spectral range of $F_1$ can be adjusted to be optimal for an energy transfer to the dye $F_2$ which is used as marker. Examples of pairs are:

| $F_1$ | $F_2$ |
|---|---|
| a) Polymer (IIa) | TRITC |
| b) Cyanine (IIIb) with $X = Y = O, R^7 = H,$ $R^8 = R^9 = C_{18}H_{37}$ | TRITC or FITC |
| c) Cyanine (IIIa) with $X = Se, Y = S,$ | FITC or TRITC |

-continued

| $F_1$ | $F_2$ |
|---|---|
| $R^7 = CH_3, R^8 = R^9 = C_{18}H_{37}$ | |

TRITC = tetramethylrhodamine isothiocyanate
FITC = fluorescein isothiocyanate.

The increase in the sensitivity of fluorescence-spectroscopic detection in the optical biosensor according to the invention is achieved, as described, by introducing a maximum possible dye concentration $F_1$ into the LB film and thus several molecules $F_1$ achieving the "Förster radius" which is necessary for the energy transfer to a molecule $F_2$ bound to the film. This construction, to introduce a maximum possible dye density $F_1$ in the LB film system besides the receptor, permits, in contrast to the detection methods based on energy transfer hitherto known, a much more favourable exploitation of this measurement principle and thus a distinctly increased sensitivity because a much larger number of dye molecules can be present per receptor molecule than in the case of a direct fluorescent labelling of the receptor molecule.

Another consequence of the use of all the dye molecules $F_1$ lying within the Förster radius of $F_2$ is that not only the lateral distribution of $F_1$ within the topmost LB films but also the concentration of $F_1$ in the underlying films is of crucial importance. For this reason, the measurement principle is restricted to films with an effective film thickness of up to about 100 Å, because underlying molecules $F_1$ are no longer able, after excitation by light, to transfer their energy to a sufficient extent to the dye $F_2$, which is then too far away, and would predominantly interfere with the signal to be detected, namely the light emission of wavelength $\lambda_3$ of the dye $F_2$ excited by transfer, owing to their own fluorescence with the wavelength $\lambda_2$, and unnecessarily reduce the sensitivity of detection.

For this reason, only LB film technology and chemisorption are suitable for producing thin films (100 Å or below) which contain $F_1$. This is because even the method of spin-coating which is widely used in thin-film technology involves problems with minimum film thicknesses of 200 to 500 Å. Compared with the application of thin films by chemisorption, the LB technique has the advantage that the composition of the films can be adjusted in a very defined manner, which is of crucial importance for producing reproducible surfaces for sensors.

The donor dye $F_1$ and the abovementioned active sites for binding of a biomolecule can, in this connection, also be located in different LB films which are arranged in sequence. The total number of LB films effective for the sensor principle varies within the numerical range from 1 to 10.

The optical biosensor according to the invention also includes mobile, fluorescent molecules which contain the dye component $F_2$ and which are reversibly bound to the receptor molecules anchored firmly in the LB film. Only in the simplest case, namely the determination of a self-fluorescent analyte, which thus acts as $F_2$, is this component unnecessary because $F_2$ and ligand are identical and represent the analyte. On the one hand, the binding sites of the receptors on the LB film can be saturated by fluorescent-labelled derivatives or analogues of the analyte molecule, and these can then be displaced competitively by the analyte on contact with the sample solution. On the other hand, however, also possible is a sandwich immunoassay in which a second type of receptors, for example antibodies, bind either to the complex between the first receptor and the analyte or to a molecular region on the analyte which is not involved in the binding to the first receptor. These methods of solid-phase immunoassays are in principle state of the art and described, for example, in the monograph P. Tijssen, Practice and Theory of Enzyme Immunoassays (R. H. Burdon, Ph. H. van Knippenberg, editors) Elsevier, Amsterdam 1985.

EXAMPLE 1

Preparation of an Amphiphilic Fluorescent Dye 1.51 g (5 mmol) of octadecane acid chloride in 5 ml of dry chloroform were added dropwise to 1.53 g (5 mmol) of 7-diethylamino-3-(p-aminophenyl)coumarin and 0.61 g (5 mmol) of triethylamine in 10 ml of dry chloroform while cooling in an ice bath. The mixture was then stirred at 0°–5° C. for one hour and at room temperature for 5 hours. The mixture was washed first with dilute sodium hydroxide solution and finally with water. The crude product was precipitated twice from chloroform with petroleum ether 60°/70° C.

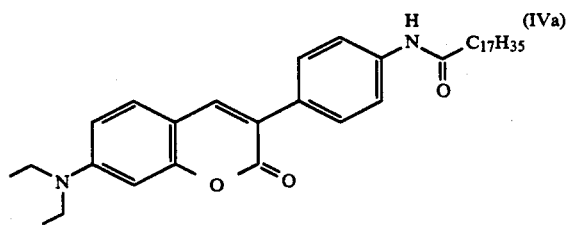
(IVa)

64% of the theoretical yield of the product of the above formula with a melting point of 159° C. were obtained.

$^1$H-NMR (CDCl$_3$, int. TMS): $\delta = 7.66$–6.52 (multiplet, aromatic protons); 3.42 (—CH$_2$CH$_3$); 2.35 (—COCH$_2$C$_{16}$H$_{33}$); 1.22 (—CH$_2$C$\underline{H}_3$); 1.7–0.8 (—COCH$_2$C$_{16}$$\underline{H}_{33}$).

Compounds IVb to IVi which are listed hereinbefore were also prepared in an analogous manner. Some spectroscopic data are compiled in Tab. 1.

TABLE 1

| | Spectroscopic data on amphiphilic dyes | | |
|---|---|---|---|
| | Spectroscopic data in CH$_2$Cl$_2$ | | |
| Formula | Exc.$_{max}$ $\lambda$ (nm) | Em.$_{max}$ $\lambda$ (nm) | $\Delta$ Stokes (nm) |
| IVa | 406 | 476 | 70 |
| IVe | 528 | 549 | 21 |
| IVf | 475 | 511 | 36 |
| IVg | 531 | 585 | 54 |
| IVh | 460 | 495 | 35 |
| IVi | 368 | 452 | 84 |

EXAMPLE 2

Preparation of a Polymerizable Fluorescent Dye 0.52 g (5 mmol) of methacryloyl chloride in 5 ml of dry chloroform was added dropwise to 1.53 g (5 mmol) of 7-diethylamino-3-(p-aminophenyl)coumarin and 0.61 g (5 mmol) of triethylamine in 10 ml of dry chloroform while cooling in an ice bath. The mixture was then stirred at 0°–5° C. for one hour and at room temperature for 5 hours. The mixture was washed first with sodium hydroxide solution and finally with water until free of salts and was concentrated to dryness. Yield: 1.6 g corresponding to a theoretical yield of 86% of the product of the formula VIa, which is detailed below (Tab. 2), with a melting point of 193°–195° C.

$^1$H-NMR (CDCl$_3$, int. TMS): δ=9.43 (NH), 7.77–6.49 (multiplet, arom. protons); 5.86 and 5.47 (H$_2$C=); 3.44 (—CH$_2$CH$_3$); 2.04 (=C—CH$_3$); 1.22 (—CH$_2$CH$_3$).

The compounds VIb to VIf which are likewise listed in Tab. 2 were also prepared in an analogous manner. Some spectroscoic data are compiled in Tab. 2.

TABLE 2

Spectroscopic data on polymerizable fluorescent dyes

| Formula | Spectroscopic data in CH$_2$Cl$_2$ | | |
|---|---|---|---|
| | Exc.$_{max.}$ λ (nm) | Em.$_{max.}$ λ (nm) | ΔStokes (nm) |
| 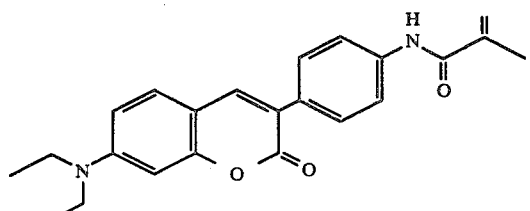 VIa | 395 | 475 | 80 |
| 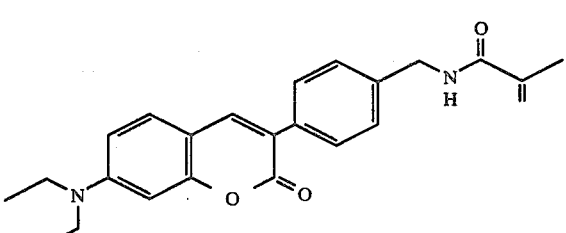 VIb | 401 | 475 | 74 |
| 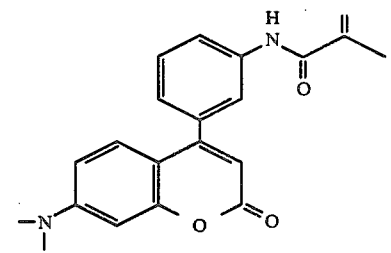 (VIc) | 382 | 491 | 110 |
| 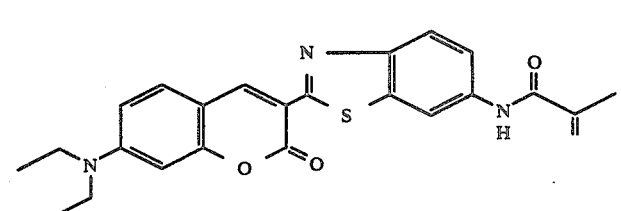 (VId) | 456 | 507 | 51 |
| 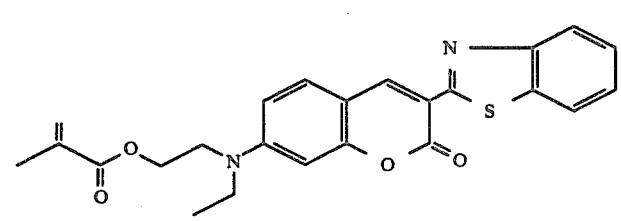 (VIe) | 528 | 546 | 17 |

TABLE 2-continued

Spectroscopic data on polymerizable fluorescent dyes

| Formula | Spectroscopic data in $CH_2Cl_2$ | | |
|---|---|---|---|
| | $Exc._{max.}$ λ (nm) | $Em._{max.}$ λ (nm) | ΔStokes (nm) |
| (VIf) 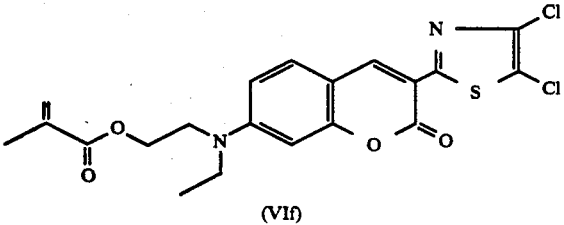 | 450 | 496 | 46 |

EXAMPLE 3

Preparation of a Polymer Containing a Fluorescent Dye 6.77 g (20 mmol) of octadecyl methacrylate, 4.00 g (20 mmol) of (2,2-dimethyl-1,3-dioxolan-4-yl)-methylenemethacrylate and 1.51 g (4 mmol) of the dye monomer of Example 2 were dissolved in 90 ml of absolute dioxane and, after addition of 1.44 g (0.2 mol-%) of azobis(isobutyronitrile), heated while stirring to 65°–70° C. and kept at this temperature for 16 hours. After cooling, the polymer was precipitated from the reaction solution by introducing it into water. The polymer was purified by dissolving in chloroform and precipitating in methanol twice.

3.93 g of a yellowish green polymer were obtained and were characterized by gel permeation chromatography in $CH_2Cl_2$. Simultaneous detection of refractive index and UV spectroscopy provided identical molecular weight distribution curves so that uniform incorporation of the fluorescent dye in the polymer was ensured. The molecular mass values calculated by comparison with a polystyrene standard were $M_n=64,000$ and $M_w=1,290,000$, corresponding to a non-uniformity of 18.1.

All the methacrylate copolymers were prepared by this general preparative procedure.

EXAMPLE 4

Preparation of a Film Element Containing Fluorescent Dye a) Polymeric dye

A slide made of float glass was cleaned by treatment with $H_2O_2/H_2SO_4$ and immersed to a depth of 30 mm in the aqueous subphase of a Langmuir film balance (KSV 2200) at 20° C. 150 μl of a solution of the compound of the formula (IIa) in chloroform (1 mg/ml) were spread on the water surface. After the film had been compressed to a surface pressure of 25 mN/m, three monomolecular layers of polymer were transferred onto the slide by successive emergence and immersion (speed of dipping: 10 mm/min). In this connection, the final film was transferred on emergence. The support was subsequently dried in the air. The dye film was removed from one side of the support by cleaning with chloroform.

b) Polymer containing dispersed monomeric dye

Used in place of the solution of the dye-containing polymer of the formula (IIa) was a mixture of the polymer of the formula (V), 1 mg/ml, and of the monomeric amphiphilic dye of the formula (IIb) with X=Y=O, n=18, $R^7$=H, $R^8$=$R^9$=$C_{18}H_{37}$, 1 mg/ml, in the ratio 19:1.

c) Polymer containing dispersed dye which forms Scheibe-aggregates

A mixture of the polymer of the formula (V), 1 mg/ml, and of the dye of the formula (IIIb), with X=Se, Y=S, $R^8$=$R^9$=$C_{18}H_{37}$, $R^2$=$CH_3$, 1 mg/ml, in the ratio of 1:1 by weight, was picked up.

EXAMPLE 5a

Adsorption of Fluorescent Dyes onto a Film Element and Observation of Fluorescent Energy Transfer A film element produced as in Example 4 was dipped in a solution of $10^{-7}$ mol/l fluorescein in phosphate buffer, pH 7.0, for 5 min. A fluorescent spectrum was recorded before and after the experiment. The emission spectrum shifted towards the maximum of fluorescein.

EXAMPLE 5b

Production of a Film Element Containing Fluorescent Dye

A glass support which had been cleaned by ultrasonic treatment in an aqueous detergent solution and subsequently rinsed by ultrasonic treatment with pure water and further ultrasonic treatment (5 min) in approx. $5 \times 10^{-2}$N NaOH and by spraying with pure water under a pressure of 5 atm, and had then been dried, was rendered hydrophobic by exposure to hexamethyldisilazane in a desiccator (30 min at 60° C. under water pump vacuum). After this treatment, the glass support was briefly dipped in water and, after removal from the water, its surface was carefully sucked off. Two films of cadmium arachidate were transferred onto this support by the LB technique by immersion and emergence of the support.

The subsequent film of fluorescent dye (VII)=(IIIa) with X=Y=O, $R^7$=H, $R^8$=$R^9$=$C_{18}H_{37}$ was prepared and transferred in different organisation, i) as monomer of the dye and ii) as Scheibe-aggregates (J-aggregates) of the dye.

i) Monomer of the dye (VII)

A monomolecular film on water was generated by spreading a solution which contains (VII), methyl arachidate, arachic acid and hexadecane in the molar ratio 1:2:18:20 in chloroform.

ii) Scheibe-aggregates of the dye (VII)

A monomolecular film on water was generated by spreading a solution of (VII) and hexadecane in the molar ratio 1:1 in chloroform.

The following construction of the film element is identical for monomer and Scheibe-aggregates. After compression of the film to a thrust of 20 mN/m and storage for 10 min at constant thrust, the film was transferred to the support by contacting the support virtually horizontally with the monofilm. The support was then completely immersed in the water, the remaining film of dye was removed, and a monofilm of stearic acid was formed by spreading a $10^{-3}$M solution in chloroform and compression to 20 mN/m. The support was then covered with a film of stearic acid by vertical emergence. Finally, the support was coated with a mixed film of dioctadecyldimethyl-ammonium bromide and methyl stearate in the molar ratio 1:1 by virtually horizontal contacting and complete immersion of the support, and assembled under water with a cuvette element to give a fluorescence cuvette in a manner known to the skilled worker (see P. Fromherz, Biochim. Biophys. Acta. 323 (1973) 326-334).

EXAMPLE 5c

A film element produced as in Example 5b was brought into contact with an aqueous solution of the analyte (VIII) (formula see below) in a $10^{-4}$M phosphate buffer, pH=7.0, by replacing the aqueous medium without exposing the surface of the film element to air. The binding of the dye to the surface of the film element results in the fluorescence intensity of (VII) being reduced in the case of the Scheibe-aggregates as a function of the concentration of the analyte in the adjoining solution and the time after setting up contact. In the case of a $10^{-7}$M solution of (VIII) the intensity of emission at 404 nm and excitation at 366 nm after 90 min is 33% of the intensity in the absence of (VIII), in the case of a $10^{-10}$M solution 85%.

As expected, this quenching effect is observed to depend distinctly on the distance when by incorporation of a double film of cadmium stearate between the stearic acid film which is enlarged in contact with the dye film from the surface of the film element. The intensity of emission from the Scheibe-aggregate at 404 nm for a $10^{-7}$M solution of (VIII) is then 90% of the intensity observed in the absence of (VIII).

The binding of the analyte (VIII) to the surface of the film element can also be detected by measuring the fluorescence of (VIII) at 510 nm. Direct excitation (emission of the analyte) is possible at 470 nm, whereas the excitation of (VII) and subsequent energy transfer leads to a maximum emission of the analyte when it takes place at 366 nm (monomer) or 402 nm (Scheibe-aggregates). The ratio of the fluorescence intensities at 510 nm after indirect excitation and energy transfer ($I_{VII}$) and on direct excitation of the bound analyte ($I_{VIII}$) is the enhancement factor and can be determined from the excitation spectrum of the emission at 510 nm. The following are found for a) Monomers:

$I_{VII}/I_A = 3$ for $10^{-7}$M solution of (VIII)

$I_{VII}/I_A = 35$ for $10^{-8}$M solution of (VIII)

b) Scheibe-aggregates:

$I_{VII}/I_A = 380$ for $10^{-8}$M solution of (VIII)

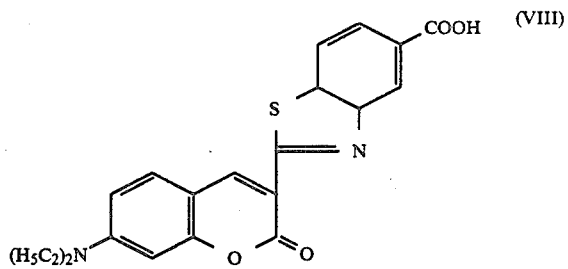

EXAMPLE 6

Adsorption of Fluorescent-Labelled Protein to a Film Element and Observation of Fluorescence Energy Transfer A 50 μl-drop of a solution of lectin concanavalin A (1 mg/ml) labelled with tetramethylrhodamine isothiocyanate (TRITC) was placed on a film element produced as in Example 4, and a second, untreated slide of the same size was pressed on in such a way that the liquid was distributed uniformly and without air bubbles on the Langmuir-Blodgett (LB) film. After an exposure time of one hour, the two supports were separated and the coated one was washed three times with aqueous phosphate buffer, 10 mmol/l, pH 6.8. A fluorescence spectrum was then recorded and compared with that of a film element not treated with protein. An additional band of the TRITC emission was detected. When two to six dye-free layers were applied on top of the dye-containing LB film, the intensity of this band decreases as a function of the film thickness as far as zero.

EXAMPLE 7 (FOR COMPARISON)

Preparation of Film Elements Using Alternative Techniques a) Smear technique

50 μl of a solution of the polymer (IIa), 1 mg/ml, in chloroform were placed on a slide. A second slide was used to smear the dye solution as uniformly as possible on the first. 50 μl of TRITC-ConA were then adsorbed, as described in Example 6, on this dye layer, and the fluorescence was measured. Besides the very intense band of (IIa) the fluorescence of TRITC cannot be detected unambiguously.

b) Spin-coating technique 0.0193 to 0.244 mg of the polymer (IIa) was dissolved in 0.25 to 1.5 ml of chloroform or dimethylformamide and put onto a cleaned glass support of 10 cm diameter using a spin-coater. Fluorescence measurements on the resulting glass plates showed a very heterogeneous distribution of dye density so that it was not possible to make any measurements of energy transfer.

EXAMPLE 8

Measurement of the Limiting Sensitivity of the Förster Energy Transfer System

A film element (donor dye) produced as in Example 4 was additionally coated first with two layers of the polymer (V) and then when one layer of the polymer (V) to which a defined amount of an amphiphilic acceptor dye is added. The fluorescence was measured on this film element. The amount of acceptor dye was varied in order to establish the limiting concentration at which the fluorescence of this substance was still just detectable. The following table presents these values for various systems:

| Donor dye | Acceptor dye | Limiting concentration $[10^{-15} \text{ mol/mm}^2]$ |
|---|---|---|
| from 4a | ($C_{18}$ rhodamine) | 3 |
| from 4b | | 0.3 |
| from 4c | | 0.3 |
| from 4c | ($C_{18}$ aminofluorescein) | 3 |

EXAMPLE 9

Specific Binding of a Mannoside to Concanavalin A

In analogy to Example 4 a film element was prepared by transferring a mixed monolayer consisting of compound (IIa) and succinimidyl stearate (95:5 w/w). On top of this a solution of unlabelled Concanavalin A (1 mg/ml, dissolved in 0.01 mol/l phosphate buffer pH 6.8 containing 1 mmol/l $CaCl_2$, 1 mmol/l $MnCl_2$ and 0.01% Triton X-100) was incubated for 1 hour at room temperature (see Example 6). The element was washed with 0.5 ml of the same buffer; 50 μl of a solution (0.1 mg/ml dissolved in the above buffer) of the TRITC-mannoside (IX) were then applied, and the film element was covered up again. As a blank control, an equal amount of bovine serum albumin was used instead of Con A. A comparison of the two film elements' fluorescence spectra showed that when using Con A the rhodamine emission at 580 nm (from IX) is about fivefold stronger than the coumarin emission at 495 nm (from IIa). When using bovine serum albumin there is almost no rhodamine emission (less than 1/20) visible in comparison with a strong coumarin emission.

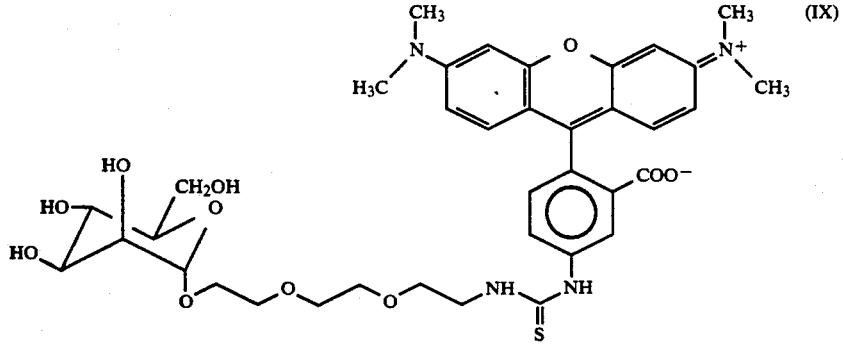

(IX)

What is claimed is:

1. A process for the detection of analyte molecules in a sample comprising providing a sensor consisting of
   a) a solid support,
   b) a single layer or multi-layer Langmuir-Blodgett (LB) film attached to the surface of said support a),
   c) at least one fluorescent dye $F_1$ which is located in the top layer or in case of a multi-layer Langmuir-Blodgett film, in at least one of the top four layers of the Langmuir-Blodgett film,
   d) a first receptor molecule which is capable of specific binding with said analyte molecule and which is bonded covalently or by absorption in or on the topmost layer of the Langmuir-Blodgett film, and
   e) exposing said sensor to said sample and a mobil fluorescent dye $F_2$ whose excitation band overlaps sufficiently for an energy transfer with the emission band of said dye $F_1$ and which
      e1) is covalently bonded to a second receptor molecule which competes with said analyte molecules for specifically binding to said first receptor molecule d) or which
      e2) is covalently bonded to a third receptor molecule which is able to bind to a complex composed of the first receptor molecule d) and said analyte molecule,
   where the second molecule or the complex of the analyte molecule and the third receptor molecule are initially not bound to the Langmuir-Blodgett film,
   and detecting a change in the level of fluorescence energy transfer in response the said exposing step.

2. A sensor for the detection of analyte molecules based on fluorescence energy transfer (Forster transfer) consisting of
   a) a solid support,
   b) a single layer or multi-layer Langmuir-Blodgett film (LB) attached to the surface of said support a),
   c) at least one fluorescent dye $F_1$ which is located in the top layer or in case of a multi-layer Langmuir-Blodgett film, in at least one of the top four layers of the Langmuir-Blodgett film,
   d) a receptor molecule which is capable of specific interaction with a ligand molecule and which is bonded covalently or by adsorption in or on the topmost layer of the Langmuir-Blodgett film.

3. A sensor according to claim 2 wherein the solid support used is composed of glass, quartz glass, Li niobate, zinc selenide, porcelain, semi-conductor materials, a metal, a plastic or a metallized plastic.

4. A sensor according to claim 3, wherein the solid support used is composed of glass, quartz glass, silicon, plastic or a metallized plastic.

5. A sensor according to claim 2, wherein the Langmuir-Blodgett film consists of a polymer.

6. A sensor according to claim 5, wherein said dye $F_1$ is covalently bonded to the polymer.

7. A sensor according to claim 2, wherein the dye $F_1$ is spread together with an amphiphilic matrix.

8. A sensor according to claim 2, wherein, in the case of a multi-layer Langmuir-Blodgett film the dye $F_1$ is located in at least one of the two upper layers of the LB film.

9. A sensor according to claim 2, wherein the receptor molecule is attached covalently to the topmost layer of the LB film.

10. The sensor of claim 9, wherein the receptor molecule d) is attached covalently via a spacer molecule to the topmost layer of the LB film.

11. The sensor of claim 2, wherein the receptor molecule d) is located onto the topmost layer of the film via a hydrophobic membrane anchor.

12. Sensor of claim 7 is which the dye $F_1$ forms Scheibe-aggregates.

* * * * *

UNITED STATES PATENT AND TRADEMARK OFFICE
CERTIFICATE OF CORRECTION

PATENT NO. : 5,194,393

DATED : March 16, 1993

INVENTOR(S) : Hugl, et al.

It is certified that error appears in the above-identified patent and that said Letters Patent is hereby corrected as shown below:

Col. 22, line 18  After " Langmuir-Blodgett " delete " film " and after " (LB) " insert -- film --

Signed and Sealed this

Thirtieth Day of August, 1994

Attest:

BRUCE LEHMAN

*Attesting Officer*   Commissioner of Patents and Trademarks